(12) United States Patent
End et al.

(10) Patent No.: US 7,081,536 B2
(45) Date of Patent: Jul. 25, 2006

(54) ISOXAZOLINE DERIVATIVES AS P N LIGANDS

(75) Inventors: Nicole End, Oberwil (CH); Catherine Stoessel, Stetten (FR); Ulrich Berens, Binzen (DE); Pier Giorgio Cozzi, Bologna (IT)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 4 days.

(21) Appl. No.: 10/485,839

(22) PCT Filed: Aug. 1, 2002

(86) PCT No.: PCT/EP02/08588

§ 371 (c)(1),
(2), (4) Date: Feb. 4, 2004

(87) PCT Pub. No.: WO03/014133

PCT Pub. Date: Feb. 20, 2003

(65) Prior Publication Data

US 2004/0171841 A1 Sep. 2, 2004

(30) Foreign Application Priority Data

Aug. 9, 2001 (IT) .......................... MI2001A1758

(51) Int. Cl.
C07D 263/08 (2006.01)

(52) U.S. Cl. ..................... 548/112; 548/237; 548/215; 548/402; 548/412; 548/416; 548/469; 548/490; 548/517

(58) Field of Classification Search ................ 548/112, 548/237, 215, 402, 412, 416, 469, 490, 517; 514/374, 414, 443; 549/6
See application file for complete search history.

(56) References Cited

U.S. PATENT DOCUMENTS 5,140,034 A * 8/1992 Baker et al. ................ 514/364
5,693,820 A 12/1997 Helmchen et al. .......... 548/101

FOREIGN PATENT DOCUMENTS

| DE | 424 3030 | | 6/1994 |
| DE | 4243030 A1 | * | 6/1994 |
| EP | 0780157 | | 6/1997 |
| WO | 00/06556 | | 2/2000 |

OTHER PUBLICATIONS

Tietze, Lutz F. and Klaas Lohmann, "Synthesis of Novel Chiral Thiophene-, Benzothiophene- and Benzofuran- Oxazoline Ligands and their Use in the Enantioselective Pd-Catalyzed Allylation," vol. 12, pp. 2083-2085, especially p. 2083, printed Feb. 12, 2002.*

Chem. Abstr. 120:77192 for Kelarev et al., "Synthesis of azoles and diazoles containing 1-methylindole Fragments.", (1993), vol. 36, No. 3, pp. 49-55.
Chem. Abstr. 95:169050 for Kelarev et al., "Preparation of 2-substituted Δ2-oxazolines from indolyl-carboxylic acid imino ester hydrochlorides.", (1981), vol. 26, No. 4, pp. 457-458.
G. Helmchen et al., Acc. Chem. Res., (2000), vol. 33, pp. 336-345.
Kwong et al., Organometallics, (2001), vol. 20, pp. 2570-2578.

* cited by examiner

Primary Examiner—Kamal A. Saeed
Assistant Examiner—Susannah Chung
(74) Attorney, Agent, or Firm—Kevin T. Mansfield

(57) ABSTRACT

The invention relates to novel ligands of the phosphanyl-benzothiophenyl-dihydroisoxazoline, phosphanyl-dihydrooxazolyl-indole and phosphanyl-dihydrooxazolyl-benzofuran type, especially compounds of formula I

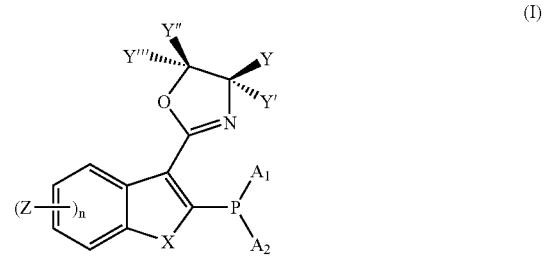

(I)

and mixtures of such compounds, wherein
X is oxygen, sulfur, selenium or NQ, wherein Q is unsubstituted or substituted aryl, or alkyl or substituted alkyl;
n is 0, 1, 2, 3 or 4;
$A_1$ and $A_2$ are each an organic radical capable of bonding to phosphorus, especially unsubstituted or substituted alkyl, unsubstituted or substituted aryl, unsubstituted or substituted heterocyclyl, unsubstituted or substituted cycloalkyl, or —N(D)$_2$ wherein $D_2$ is alkyl or substituted alkyl; or $A_1$ and $A_2$ together with the bonding phosphorus atom form a ring, which may be unsubstituted or substituted;
Y, Y', Y" and Y''' are each independently of the other hydrogen or alkyl, substituted alkyl, unsubstituted or substituted aryl, or unsubstituted or substituted heterocyclyl, at least one of the radicals Y, Y', Y" or Y''' being one of the mentioned radicals with the exception of hydrogen; and
Z, when present, is a substituent, it being possible when a plurality of substituents Z is present for those substituents to be selected independently of one another, and to processes for their preparation, to novel precursors and intermediates, to complexes with the said ligands, to their preparation and to their use as catalysts in organic synthesis (especially asymmetric organic synthesis).

13 Claims, No Drawings

ISOXAZOLINE DERIVATIVES AS P N LIGANDS

This application is a 371 National Stage of PCT/EP 02/08588 filed Aug. 1, 2002.

SUMMARY OF THE INVENTION

The invention relates to novel ligands of the phosphanyl-benzothiophenyl-dihydroisoxazoline, phosphanyl-dihydrooxazolyl-indole and phosphanyl-dihydrooxazolyl-benzofuran type, to processes for their preparation, to novel precursors and intermediates, to complexes with the said ligands, and to their preparation and their use as catalysts in organic synthesis.

BACKGROUND TO THE INVENTION

Mixed donor ligands, especially P,N ligands, form a class of not too strongly binding ligands that contain a combination of hard and soft donor atoms in a molecule and consequently the resulting metal complexes exhibit unique reactivity. The utility of the P,N ligands has been demonstrated in a whole range of asymmetric catalysis reactions, such as asymmetric allylic alkylation, hydrogenation, transfer hydrogenation, hydrosilylation, hydroboration, hydroformylation, Diels-Alder reaction, Grignard cross-coupling reaction, Heck reaction and conjugate-addition reaction, as well as in copolymerisation, terpolymerisation, catalytic amination and cross-coupling (for references see F. Y. Kwong, K. S. Chan, Organometallics 20, 2570–2578 (2001), and G. Helmchen, A. Pfaltz, Acc. Chem. Res. 33, 336 (2000)).

It has been found that a critical factor for selectivity in enantioselective catalyses with P,N ligands is the "bite angle" P-M-N (coordination angle between M, which is the complexed metal, and the ligand atoms phosphorus and nitrogen). Phosphinoaryloxazoline ligands (PHOX ligands) are known (see G. Helmchen, A. Pfaltz, Acc. Chem. Res. 33, 336 (2000)).

The aim of the present invention is the provision of a new class of ligands which, by virtue of their specific binding angle and the possibility of varying the electron donor properties, enable especially advantageous catalysts to be prepared. A particular objective inter alia is to achieve a higher enantiomeric excess (ee) in the catalysis and to obtain high yields.

GENERAL DESCRIPTION OF THE INVENTION

The invention relates to compounds of formula I

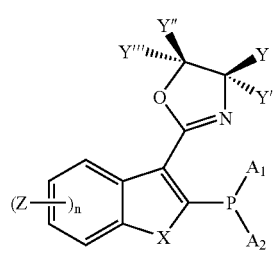

(I)

especially of formula IA or IB

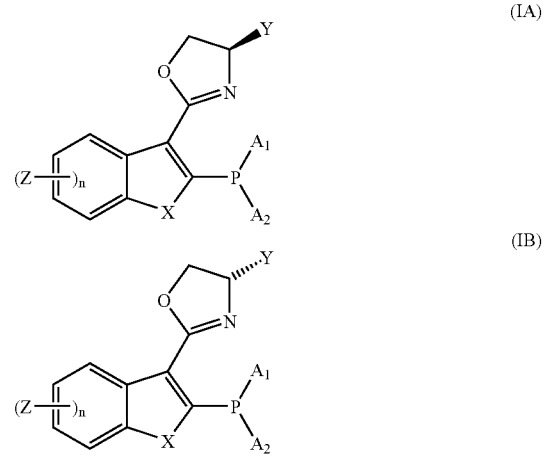

and mixtures thereof, wherein

X is oxygen, sulfur, selenium or NQ, wherein Q is unsubstituted or substituted aryl, or alkyl or substituted alkyl;

n is 0, 1, 2, 3 or 4;

$A_1$ and $A_2$ are each an organic radical capable of bonding to phosphorus, especially unsubstituted or substituted alkyl, unsubstituted or substituted aryl, unsubstituted or substituted heterocyclyl, unsubstituted or substituted cycloalkyl, or —N(D)$_2$ wherein $D_2$ is alkyl or substituted alkyl; or $A_1$ and $A_2$ together with the bonding phosphorus atom form a ring, which may be unsubstituted or substituted; Y, Y', Y" und Y'" are each independently of the other hydrogen or alkyl, substituted alkyl (including aryl-lower alkyl wherein the aryl radical is unsubstituted or substituted, and heterocyclyl-lower alkyl wherein the heterocyclyl radical is unsubstituted or substituted), unsubstituted or substituted aryl, or unsubstituted or substituted heterocyclyl, at least one of the radicals Y, Y', Y" or Y'" being one of the mentioned radicals with the exception of hydrogen; and Z, when present, is a substituent, it being possible when a plurality of substituents Z is present for those substituents to be selected independently of one another.

The invention relates also to a process for the preparation of compounds of formula I, especially of formula IA or IB, or mixtures thereof.

The invention relates also to complexes of transition metals comprising compounds of formula I, especially of formula IA or IB, or mixtures thereof, as ligands.

A further aspect of the invention relates to the use of complexes of compounds of formula I, especially of formula IA or IB, or mixtures thereof, as catalysts in organic synthesis, and to processes for the preparation of organic compounds in which those catalysts are used.

Complexes with ligands of formula I, especially of formula IA or IB, and also mixtures thereof, can be used for a large number of syntheses. In comparison with other ligands, such as PHOX ligands, they give rise to high yields and, when the pure isomers of formula I, especially of formula IA or IB, are used, also high stereoselectivity, for example a high enantiomeric excess. A further advantage is that by varying X, ligands of formula I, especially of formula IA and/or IB, can additionally be electronically modulated and thus, for example by experimental comparison or computer modelling, the optimum ligand for a specific reaction can be ascertained and used.

DETAILED DESCRIPTION OF THE INVENTION

Unless indicated to the contrary, the general terms (including the reactions and reaction conditions) used hereinabove and hereinbelow preferably have the following meanings—these specific definitions and descriptions of reactions can be used independently of one another instead of the general terms mentioned hereinabove and hereinbelow, resulting in preferred embodiments of the invention:

The prefix "-lower" or "lower" indicates that the radical in question contains preferably up to 7 carbon atoms, especially up to 4 carbon atoms. Lower alkyl is therefore preferably $C_1$–$C_7$-alkyl, especially $C_1$–$C_4$alkyl, and may be unbranched or branched one or more times, insofar as possible, and is e.g. methyl, ethyl, n-propyl, isopropyl, n-butyl, isobutyl, sec-butyl, tert-butyl, pentyl or hexyl.

Mixtures of compounds of formula I, especially of formulae IA and IB, compounds of formula II, especially of formulae IIA and IIB, compounds of formula V, especially of formulae VA and VB, and compounds of formula VI, especially of formulae VIA and VIB, are especially mixtures of diastereoisomers or enantiomers in any desired ratios, for example in a ratio of IA: IB of 1–3: 1–3, especially racemates, or achiral ligands of the type.

Alkyl is especially $C_1$–$C_{20}$alkyl and may be unbranched or branched one or more times. Lower alkyl is preferred.

Substituted alkyl carries especially one or more radicals, preferably from 1 to 3 radicals, which are selected independently of one another from unsubstituted or substituted aryl, as defined below, especially phenyl; unsubstituted or substituted cycloalkyl, especially as defined below, more especially cyclopropyl, cyclobutyl, cyclopentyl or cyclohexyl; unsubstituted or substituted heterocyclyl, especially as defined below; halogen, such as chlorine or fluorine; hydroxy; lower alkoxy, such as methoxy or ethoxy; phenyl-lower alkoxy, such as benzyloxy; lower alkanoyloxy, such as acetoxy; amino; N-lower alkyl- or N,N-di-lower alkyl-amino; N-phenyl-lower alkyl- or N,N-bis(phenyl-lower alkyl)-amino; carboxy; lower alkoxy-carbonyl; phenyl-lower alkoxycarbonyl; cyano; carbamoyl; guanidino; amidino; and sulfamoyl.

Halogen is especially fluorine, chlorine, bromine or iodine, unless indicated otherwise.

n is preferably 0 or 1, especially 0.

An organic radical capable of bonding to phosphorus is especially unsubstituted or substituted alkyl, unsubstituted or substituted aryl, unsubstituted or substituted heterocyclyl, unsubstituted or substituted cycloalkyl, —OD or —N(D)$_2$, wherein D is alkyl or substituted alkyl.

Unsubstituted or substituted alkyl is preferably as defined above, but, in the case of D in the radical —N(D)$_2$, substituents having active hydrogen atoms, such as hydroxy or amino, are not bonded to the carbon atom by way of which D is bonded to the nitrogen atom (unstable). Lower alkyl is preferred.

Aryl is preferably an unsaturated ring system consisting of one or more rings and having carbon as ring atom, having up to 24 ring carbon atoms, preferably having from 6 to 14 ring carbon atoms, especially phenyl, naphthyl or fluorenyl, and is unsubstituted or substituted by one or more radicals, especially up to 3 radicals, selected from nitro, lower alkyl and those mentioned for substituted alkyl. Phenyl is preferred.

Heterocyclyl is preferably an unsaturated, saturated or partially saturated mono-, di- or poly-cyclic system having preferably from 3 to 30, especially from 4 to 16, ring atoms, at least one ring atom being other than carbon, preferably up to four, especially up to three, ring carbon atoms being replaced by hetero atoms selected from oxygen, nitrogen or sulfur. Heteroaryl is unsubstituted or substituted by one or more, especially up to three, substituents selected from nitro, lower alkyl and the substituents mentioned for substituted alkyl. Heterocyclyl is especially imidazolyl, thienyl, furyl, tetrahydrofuryl, pyranyl, thianthrenyl, isobenzofuranyl, benzofuranyl, chromenyl, 2H-pyrrolyl, pyrrolyl, pyrrolinyl, pyrrolidinyl, imidazolidinyl, benzimidazolyl, pyrazolyl, pyrazolidinyl, pyranyol, thiazolyl, isothiazolyl, oxazolyl, isoxazolyl, pyridyl, pyrazinyl, pyrimidinyl, piperidyl, piperazinyl, pyridazinyl, morpholinyl, thiomorpholinyl, indolizinyl, isoindolyl, 3H-indolyl, indolyl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, benzothiophenyl, phthalazinyl, naphthyridinyl, quinoxalyl, quinazolinyl, cinnolinyl, pteridinyl, carbazolyl, β-carbolinyl, phenanthridinyl, acridinyl, perimidinyl, phenanthrolinyl, furazanyl, phenazinyl, phenothiazinyl, phenoxazinyl, isochromanyl or chromanyl, each of those radicals being unsubstituted or substituted by from 1 to 3 radicals selected from lower alkyl, lower alkoxy and halogen. Unsubstituted heterocyclyl, especially one of the radicals listed above, is preferred.

A ring formed by $A_1$ and $A_2$ together with the bonding phosphorus atom is preferably formed by the phosphorus atom and an unsubstituted or substituted trimethylene, tetramethylene or pentamethylene radical, wherein the substituents may be especially one or more, preferably up to 4, substituents selected from alkyl, preferably as defined above, especially lower alkyl, cycloalkyl, preferably as defined below, especially $C_3$–$C_8$cycloalkyl, aryl, preferably as defined above, especially phenyl, and arylalkyl, especially benzyl.

A substituent Z is preferably lower alkyl, nitro or one of the substituents mentioned above as substituents of substituted alkyl. When a plurality of radicals Z (n>1) is present, they are selected independently of one another, that is to say some or all of them can be the same or they can all be different.

Complexes comprising ligands of formula I, especially of formula IA and/or IB, more especially one of the two, are especially complexes with transition metals, more especially of groups III to XII of the Periodic Table of the Elements, the lanthanides or the actinides, especially of groups IV to XII, especially with rhodium, ruthenium, palladium, platinum, iridium, nickel or cobalt.

Such complexes can be prepared according to standard methods using solutions of the ions or using complexes of transition metals, for example rhodium complexes by reaction with [(COD)RhCl]$_2$ (COD=cyclooctadiene), [(COD)$_2$Rh]$^+$G$^-$, wherein G$^-$ is BF$_4^-$, SbF$_6^-$, PF$_6^-$ or CF$_3$SO$_3^-$, with [Rh(1,5-COD)$_2$]ClO$_4$, [Rh(COD)(acetyl acetonate)] or the like; and ruthenium complexes by reaction with [RuCl$_2$(C$_6$H$_6$)]$_2$, [RuCl$_2$(PPh$_3$)$_3$] (Ph=phenyl) or the like. The resulting complexes may contain, in addition to counterions, also further ligands, for example benzene or the like.

Preparation is carried out by standard methods, for example in the presence of organic solvents under an inert gas atmosphere, such as nitrogen or argon, at atmospheric pressure at a temperature of from 0° C. to the boiling point of the mixture (see e.g. G. Helmchen, A. Pfaltz, Acc. Chem. Res. 33, 336 (2000), and literature cited therein).

Alternatively, corresponding complexes can also be prepared in situ, for example under inert gas, such as argon, in a dried alcohol, such as isopropanol, with heating to reflux, the resulting solution containing the complex then being combined directly with the substrate and the latter being reacted catalytically.

The corresponding complexes can be employed in a large number of catalytic applications, especially (primarily using isomerically pure compounds of formula I, chiefly of formula IA or of formula IB) in asymmetric catalysis reactions, such as asymmetric allylic alkylation, hydrogenation, transfer hydrogenation, hydrosilylation, hydroboration, hydroformylation, hydroamination, Diels-Alder reaction, Grignard cross-coupling reaction, Heck reaction and conjugate-addition reaction, as well as in copolymerisation, terpolymerisation, catalytic amination and cross-coupling (for references see F. Y. Kwong, K. S. Chan, Organometallics 20, 2570–2578 (2001), and G. Helmchen, A. Pfaltz, Acc. Chem. Res. 33, 336 (2000)).

The compounds of formula I, especially of formula IA and/or IB, can be prepared according to processes known per se (but novel in respect of the novel starting materials and end products), especially as follows: for the preparation of a compound of formula I, a compound of formula II or, especially for the preparation of a compound of formula IA, a compound of formula IIA or, for the preparation of a compound of formula IB, a compound of formula IIB or, for the preparation of a mixture of compounds of formula I, especially of formulae IA and IB, a mixture of compounds of formulae II, especially IIA and IIB,

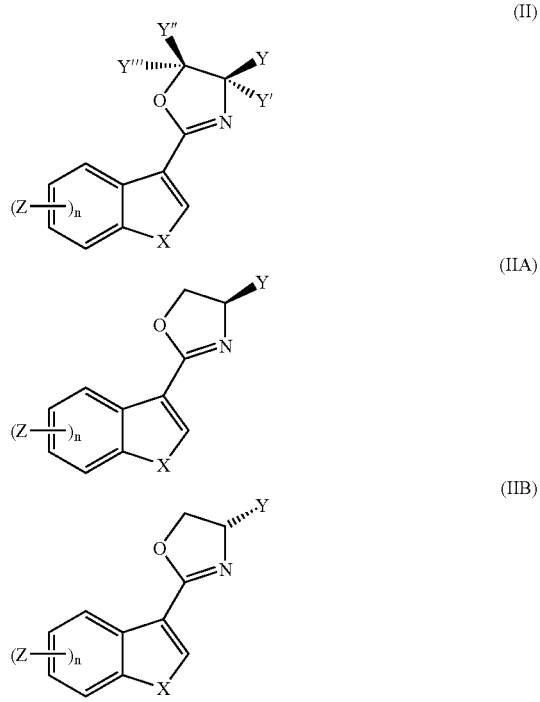

wherein Z, n, Y, Y', Y'', Y''' (when present) and X are as defined for compounds of formula I, especially of formula IA or IB, is reacted, after the addition of a metal organyl, with a compound of formula III

wherein $A_1$ and $A_2$ are as defined for compounds of formula I, especially of formula IA or IB, and L is halogen, especially chlorine or bromine, (alternatively it is also possible for the synthesis of compounds of formula I to proceed via a phosphine oxide, which is then reduced) and if desired an obtainable compound of formula I, especially of formula IA or IB, or a mixture thereof, is converted into a different compound of formula I, especially of formula IA or IB, or a mixture thereof, and/or an obtainable isomeric mixture of compounds of formula I, especially of formulae IA and IB, is separated into the individual isomers.

In the following more detailed description of the reaction conditions and the preparation of starting compounds, unless otherwise indicated the symbols $A_1$, $A_2$, n, X, Y, Y', Y'', Y''' and Z are as defined for compounds of formula I, especially of formula IA or IB.

The reaction between a compound of formula II, especially of formula IIA and/or IIB, and a compound of formula III is preferably carried out in an anhydrous medium and under anhydrous conditions (preferably Schlenk vessels), especially in aprotic organic solvents, such as ethers, especially di-lower alkyl ethers, more especially diethyl ether, or cyclic ethers, especially tetrahydrofuran, at preferred temperatures of from −80 to 40° C., especially from −78 to 25° C., a relatively low temperature preferably being used in the initial reaction between the metal organyl and the compound of formula IIA or IIB, whereas a relatively high temperature is preferably used more in the reaction of the resulting organometallic compound with the compound of formula III. Suitable metal organyls are especially organolithium compounds, such as lower alkyl-lithium, preferably butyl-lithium, such as n-butyllithium. The reaction is preferably carried out under protective gas, such as nitrogen or argon.

Conversion Reactions:

A compound of formula I, especially of formula IA or IB, can be converted into a different compound of formula I, especially IA or IB, for example by converting any substituents present into other substituents, for example by converting phenyl-lower alkoxy or lower alkanoyloxy by known methods into hydroxy, N-phenyl-lower alkyl or N,N-bis(phenyl-lower alkyl) into amino, lower alkoxycarbonyl into carboxy, or the like.

The separation of isomeric mixtures of compounds of formula I, especially of formulae IA and IB, into the individual isomers is effected by standard methods, for example by chromatographic separation over column materials having chiral surface structures, precipitation with chiral salt-forming agents, enzymatic separation of isomers (for example by modifying only one isomer, leaving the other in unmodified form) or the like, or combinations thereof.

Starting Compounds:

The starting compounds (especially of formula III) are known or are obtainable according to processes known per se, or they are commercially available.

Compounds of formula II, especially of formula IIA or IIB, or mixtures thereof can be obtained especially by reacting a compound of formula IV

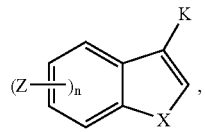
(IV)

wherein K is cyano or activated carboxy and the remaining radicals are as defined for compounds of formula I, with a β-amino alcohol of formula V (for the preparation of a compound of formula II), especially of formula VA (for the preparation of a compound of formula IIA) or of formula VB (for the preparation of a compound of formula IIB), or for the preparation of a mixture of compounds of formula II, especially of formulae IIA and IIB, with a mixture of β-amino alcohols of formula V, especially of an alcohol of formula VA and an alcohol of formula VB,

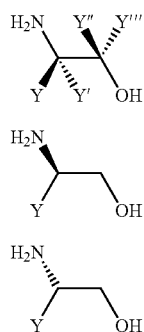

(V)

(VA)

(VB)

wherein Y, Y', Y" und Y'" are each as defined for compounds of formula I.

For the case where K is cyano (especially when X=NQ), the reaction is carried out under customary conditions for the conversion of nitrites into dihydrooxazole groups, preferably in the presence of a zinc salt, especially zinc chloride (preferably rendered anhydrous before-hand by melting), in a halogenated hydrocarbon, especially an aromatic hydrocarbon, such as chlorobenzene, with heating, preferably from 50° C. to reflux temperature, especially at reflux temperature.

For the case where K is activated carboxy (especially when X=O, S), there comes into consideration as activated carboxy especially halogen (especially preferred), acyloxy, activated hydrocarbyloxy, activated hydrocarbylthio and —N(CH₃)—OCH₃. Halogen is especially fluorine or more especially chlorine or bromine; acyloxy is preferably lower alkanoyloxy.

Activated hydrocarbyloxy or hydrocarbylthio is preferably unsubstituted or substituted lower alkyloxy, unsubstituted or substituted aryloxy (preferably having from 6 to 12 ring atoms) or unsubstituted or substituted heterocyclyloxy (preferably an unsaturated or fully or partially saturated mono- or bi-cyclic ring system having from 4 to 12 ring atoms and up to three hetero atoms selected from nitrogen, sulfur and oxygen) and is especially carbonyl esterified in the 1-position, such as lower alkoxycarbonyl, cyano or phenylcarbonyl-substituted lower alkyloxy, especially lower alkoxycarbonylmethoxy, such as ethoxycarbonylmethoxy, cyanomethoxy or phenacyloxy(Ph-CO—CH₂—O—), tert-butylthio, N-benzotriazolyloxy, N-succinimidyloxy, pyridyloxy or pyridylthio, especially 2-pyridyloxy or more especially 2-pyridylthio, or electronegatively substituted aryloxy, such as p-nitrophenyloxy, 2,4-dinitrophenyloxy, pentafluorophenyloxy or 2,4,5-trichlorophenyloxy.

The reaction is carried out under customary conditions, preferably in the presence of a tertiary nitrogen base, such as a tri-lower alkylamine, especially triethylamine, or a cyclic base containing tertiary nitrogen, such as pyridine or dimethylaminopyridine, in a suitable solvent, such as a halogenated hydrocarbon, especially a chlorinated lower alkane, such as methylene chloride, at preferred temperatures of from −20 to 30° C., especially from 0 to 30° C. Initially there is obtained an intermediate compound of formula VI (from V), especially VIA (from VA) or VIB (from VB), or a mixture thereof (from a mixture of compounds of formula V, especially of VIA and VIB),

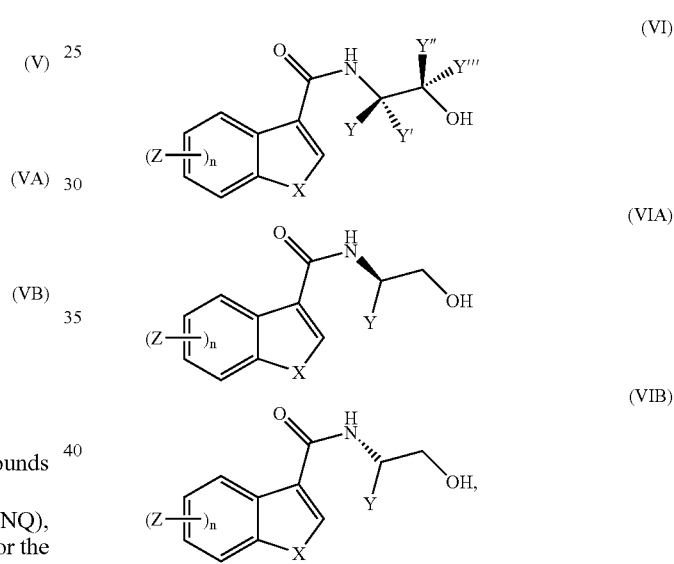

wherein the radicals are each as defined for compounds of formula I, especially IA or IB. That compound or mixture is then converted into the corresponding compound of formula II, especially of formula IIA or IIB, or a mixture thereof, in the presence of an inorganic acid halide, such as especially a phosphorus trihalide, phosphorus pentahalide or thionyl halide, such as phosphoryl chloride, phosphoryl bromide, phosphorus trichloride, phosphorus tribromide, phosphorus pentachloride, phosphorus pentabromide, thionyl chloride or thionyl bromide, either with isolation of the corresponding compound having a halogen atom in place of the hydroxy group, or with immediate further reaction. The reaction is carried out in the presence of a suitable solvent, for example a halogenated hydrocarbon, such as a halogenated lower alkane, especially dichloroethane, at elevated temperatures, especially from 50 to 80° C., e.g. at about 70° C. When the halogenated intermediate compound is isolated, it is then converted into the corresponding compound of formula II or a mixture of such compounds, especially of formula IIA and/or IIB, in the presence of a hydroxide solution, for example an alkali metal hydroxide, such as sodium hydroxide, in a suitable solvent, especially an alcohol, such as methanol or ethanol.

Compounds of formula IV wherein K is activated carboxy are obtained, for example, by standard methods; they can be obtained especially by conversion of an acid of formula VII

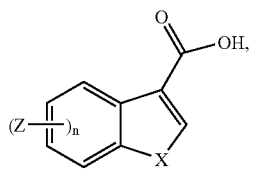
(VII)

wherein Z, n and X are as defined for compounds of formula I, by means of an organic acid halide (yielding, given a suitable reaction procedure, also the acyloxy radicals when it is an acyl halide) or preferably an inorganic acid halide (yielding the carboxylic acid halides of formula IV), especially a corresponding inorganic acid halide, such as a phosphorus trihalide, phosphorus pentahalide or thionyl halide, such as phosphoryl chloride, phosphoryl bromide, phosphorus trichloride, phosphorus tribromide, phosphorus pentachloride, phosphorus pentabromide, thionyl chloride or thionyl bromide, especially using thionyl chloride; in the presence or absence of solvents and preferably at elevated temperature, especially from 40° C. to the reflux temperature, especially under reflux. From the carboxylic acid halides of formula IV it is possible to prepare, for example, the corresponding hydrocarbylthiocarbonyl or hydrocarbyloxycarbonyl compounds of formula IV according to standard methods by reaction with the corresponding hydrocarbylthiols or hydrocarbyl alcohols, or they are reacted directly with the carboxylic acid of formula VII in the presence of coupling reagents, such as dicyclohexylcarbodiimide, if necessary in the presence of a tertiary nitrogen base, such as pyridine, N,N-dimethylaminopyridine or a tri-lower alkylamine, and, if necessary, customary solvents.

Carboxylic acids of formula VII can be obtained especially by carboxylation of a compound of formula VIII

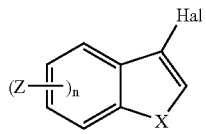
(VIII)

wherein Hal is bromine, chlorine or iodine, especially bromine or chlorine. The carboxylation is preferably carried out after conversion of the compound of formula VIII with a metal, such as especially lithium or more especially magnesium, preferably in an ether, such as a di-lower alkyl ether, e.g. diethyl ether, in the presence of an alkyl halide, such as methyl iodide, at temperatures of from 0° C. to the reflux temperature, especially from 20° C. to reflux temperature, by subsequently passing carbon dioxide through the mixture, there preferably being added an aromatic hydrocarbon, such as toluene, as solvent and the reaction preferably being carried out at temperatures of from 10 to 40° C., especially at about room temperature.

Compounds of formula VIII can be obtained especially by reaction of a compound of formula IX

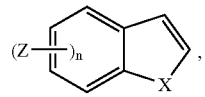
(IX)

wherein X is as defined for compounds of formulae IA and IB, and is preferably sulfur, and n and Z are as defined for compounds of formulae IA and IB, with chlorine, bromine or iodine in a suitable solvent, especially a halogenated hydrocarbon, such as chloroform, at preferred temperatures of from 10 to 40° C., especially at about room temperature.

Compounds of formula IX are known, can be prepared according to methods known per se and/or are commercially available.

Compounds of formula IV wherein K is cyano can be obtained, for example, from aldehydes of formula X

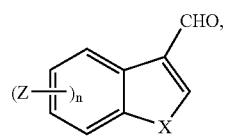
(X)

wherein X, Z and n are as defined for compounds of formulae IA and IB, X preferably being NQ, wherein Q is as defined for compounds of formula I and is especially lower alkyl, by first reacting such a compound in the presence of hydroxylamine, or a salt thereof, such as a hydrogen halide salt, especially with hydroxylamine hydrochloride, in a polar solvent, such as an alcohol, especially ethanol, in the presence of a tertiary nitrogen base, such as pyridine, preferably at elevated temperatures, for example from 25° C. to the reflux temperature, especially at reflux temperature, to form the corresponding oxime which, preferably after isolation, is dehydrated to form the corresponding cyanide, especially by means of a carboxylic acid anhydride, more especially a lower alkanecarboxylic acid anhydride, such as acetic anhydride, at elevated temperature, especially from 40 to 120° C., more especially from 70 to 90° C.

Compounds of formula X are known, can be prepared according to methods known per se or are commercially available. For example, compounds of formula X in which X is NQ, wherein Q is especially lower alkyl, can be obtained by conversion of the corresponding compound wherein X is NH, by reacting the latter with a strong base, especially an alkali metal hydride, such as sodium hydride, in a suitable solvent, such as a cyclic ether, especially THF (it also being possible for hydrocarbons, such as mineral oils, to be present) at preferred temperatures of from 0 to 50° C., especially at about room temperature, with a compound of formula Q-M, wherein M is a leaving group, especially halogen, such as bromine or iodine.

Compounds of formula V, especially VA or VB, are known or can be prepared according to processes known per se or are mostly commercially available, such as D- or L-forms of leucinol, valinol, phenylglycinol, isoleucinol, alaninol, phenylalaninol, histidinol, methioninol (all obtainable e.g. from Fluka, Buchs, Switzerland) and also tyrosinol, tryptophanol, lysinol, argininol, or glutaminol or asparaginol, each esterified by lower alkyl at the carboxy group, or serinol, cysteinol and the like.

General Reaction Conditions:

In all the starting compounds, functional groups that are not to participate in a reaction can, if necessary, be protected by protecting groups. It is characteristic of protecting groups that they are simple to remove (that is to say without undesirable secondary reactions taking place), for example by solvolysis, reduction, photolysis or alternatively under conditions analogous to physiological conditions, for example enzymatically.

The protecting groups can be introduced and removed at any suitable stage. The person skilled in the art will be familiar with the suitable protecting groups and the requirements and possibilities for their introduction and removal at different stages of the reaction.

The protection of functional groups by such protecting groups, protecting groups suitable for the protection, for example, of amino, hydroxy, mercapto, carboxy, amido or guanidino groups, reagents suitable for their introduction, suitable protecting groups and reactions for their removal will be familiar to the person skilled in the art. Examples of suitable protecting groups can be found in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, $4^{th}$ edition, Vol. 15/I, Georg Thieme Verlag, Stuttgart 1974, in H.-D. Jakubke and H. Jescheit, "Aminosäuren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974.

Where necessary, the said reactions are carried out in the absence of oxygen, and often also in the absence of carbon dioxide and/or atmospheric moisture, for example under a protective gas, such as argon or nitrogen.

Where possible, the starting compounds and intermediate compounds can also be used in the form of salts, obtained in the form of salts or converted into salts in accordance with customary processes, for example in the case of carboxy compounds into the corresponding metal salts, such as alkali metal salts, e.g. sodium or potassium salts, or alkaline earth metal salts, such as calcium salts, or salts with nitrogen bases, such as ammonium, tri-lower alkyl-ammonium, pyridinium salts or the like. Where salt formation is possible, any reference to any compound should be understood as also including the corresponding salts.

In addition to the solvents already mentioned, it is also possible to use other suitable solvents, where expedient and possible for the reaction in question. Such solvents can be selected, for example, from the following list: water, esters, e.g. lower alkyl-lower alkanoates, such as diethyl acetate, ethers, e.g. aliphatic ethers, such as diethyl ether, or cyclic ethers, such as dioxane or tetrahydrofuran, liquid aromatic hydrocarbons, such as benzene or toluene, alcohols, such as methanol, ethanol or 1- or 2-propanol, nitriles, such as acetonitrile, halogenated hydrocarbons, such as dichloromethane, chloroform or ethylene chloride, acid amides, such as dimethylformamide, bases, e.g. heterocyclic nitrogen bases, such as pyridine, carboxylic acids, such as lower alkanecarboxylic acids, e.g. acetic acid, carboxylic acid anhydrides, e.g. lower alkanoic acid anhydrides, e.g. acetic anhydride, cyclic, linear or branched hydrocarbons, such as cyclohexane, hexane or isopentane, or mixtures of such solvents or other solvents, e.g. aqueous solutions. Such solvents and solvent mixtures can also be used in working-up, e.g. by chromatography or partition. Any reference to solvents or eluants hereinabove and hereinbelow should be understood as including also mixtures of such solvents or eluants.

Wherever solvents are mentioned hereinabove and hereinbelow it is also possible, where expedient and possible, for mixtures of two or more of the mentioned solvents to be used. The person skilled in the art will know that for certain reactions such solvents or solvent mixtures must be used in anhydrous (absolute) form and that, if necessary, also the reaction vessels used must have dry surfaces.

PREFERRED EMBODIMENTS OF THE INVENTION

In the preferred embodiments of the invention mentioned below, general symbols or terms can be replaced individually, independently of one another or all together, by more specific definitions as given above, unless otherwise indicated; especially preferred embodiments of the invention are thereby defined.

The invention relates to compounds of formula I described above, especially IA or IB, and mixtures of such compounds, wherein X is oxygen, sulfur or NQ, wherein Q is alkyl;

n is 0;

$A_1$ and $A_2$ are each unsubstituted or substituted aryl; and

Y, Y', Y" and Y"' are each independently of the other hydrogen, alkyl or unsubstituted or substituted aryl, at least one of the radicals Y, Y', Y" or Y"' having one of the mentioned meanings with the exception of hydrogen.

Special preference is given to compounds of formula I, especially of formula IA, of formula IB, and mixtures of such compounds, wherein X is sulfur or NQ, wherein Q is lower alkyl, especially methyl;

n is 0;

$A_1$ and $A_2$ are each phenyl; and

Y, Y', Y" and Y"' are each independently of the other hydrogen, lower alkyl, especially isopropyl or tert-butyl, or phenyl, at least one of the radicals Y, Y', Y" or Y"' being one of the mentioned radicals with the exception of hydrogen.

The invention relates especially to pure isomers (preferably having a purity of more than 80%, especially more than 90%, more especially more than 95%, very especially more than 98%) of formula I, especially of formula IA or of formula IB, as defined in the last two paragraphs or at the very beginning.

The invention relates especially also to complexes of transition metals, especially of rhodium, ruthenium, also palladium, platinum, iridium, nickel or cobalt, which comprise as ligand a compound of formula IA or IB, as defined in the last three paragraphs, or a mixture thereof.

For the preparation of complexes there are used especially the isomerically pure compounds of formula I, especially either of formula IA or of formula IB, resulting in catalysts suitable for use as chiral catalysts for performing stereoselective reactions.

The invention relates also to novel intermediate compounds, especially those of formula II, more especially of formulae IIA and IIB, and mixtures thereof, especially the compounds of formula II mentioned in the Examples.

The invention relates especially to the compounds of formula I, especially of formula IA and/or IB, mentioned in the following Examples, to their preparation, to novel precursors and intermediates, to complexes of compounds of formula I and mixtures thereof, especially of formula IA and/or IB, and their uses or processes for the preparation of organic compounds in which those complexes are used as catalysts.

The following Examples serve to illustrate the invention but do not limit the scope thereof:

| Abbreviations: | |
| --- | --- |
| b.p. | boiling point |
| eq. | equivalent(s) |
| h | hour(s) |
| HV | high vacuum |
| min | minute(s) |
| NMR | nuclear magnetic resonance spectroscopy |
| RT | room temperature |
| THF | tetrahydrofuran |

The following page shows the reaction scheme for Examples 1 to 3:

Reaction scheme for Examples 1 to 3:

EXAMPLE 1

2-(2-Diphenylphosphanyl-benzo[b]thiophen-3-yl)-(4S)-isopropyl-4,5-dihydro-oxazoline 8a The oxazoline 7a (0.92 g, 3.83 mmol) is dissolved in 10 ml of diethyl ether in a Schlenk vessel under argon and cooled to −78° C. n-Butyllithium (1.6M in hexane, 2.63 ml, 4.20 mmol, 1.1 eq.) is added dropwise and the resulting milky suspension is stirred for 1.5 h. Chlorodiphenylphosphine is then added dropwise and the reaction mixture is stirred for a further 30 min at RT. Pentane and water are then added and the organic phase is separated off, washed with water, dried over sodium sulfate, filtered and concentrated by evaporation, yielding 8a (1.30 g, 79%) in the form of a yellow oil which crystallises under HV: $^{31}$P-NMR (124 MHz, CDCl$_3$): −12.4; $^1$H-NMR (300 MHz, CDCl$_3$): 0.81 (d, J=6.8, 3H); 0.90 (d, J=6.5, 3H); 1.62–1.70 (m, 1H); 3.88 (dd, J=7.6, 7.6, 1H); 3.95–4.04 (m, 1H); 4.16 (dd, J=8.9, 7.8, 1H); 7.28–7.49 (m, 12H); 7.65–7.69 (m, 1H); 8.57 (d, J=8.2, 1H).

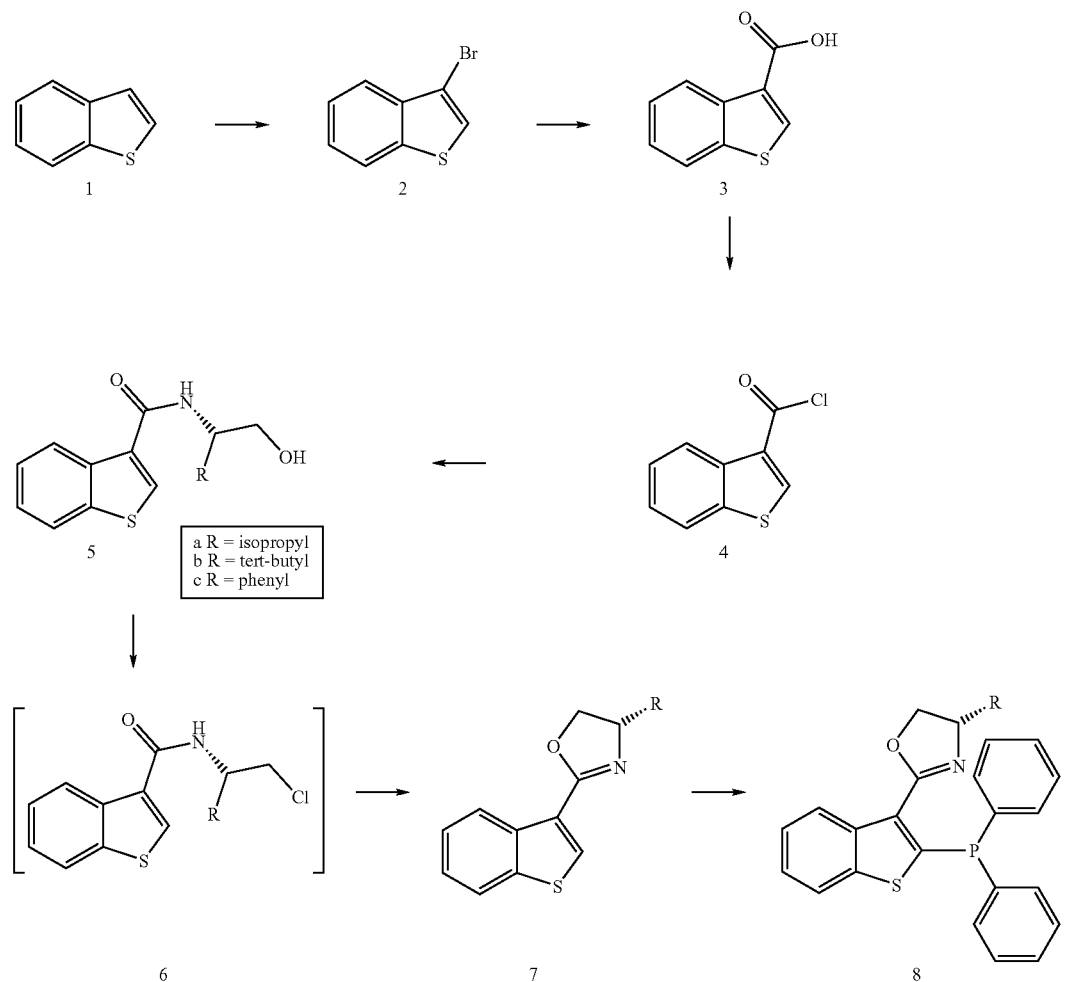

The starting materials are prepared as follows:

a) 3-Bromo-benzo[b]thiophene 2: A solution of bromine (9.1 ml, 0.176 mmol, 1.07 eq.) in 60 ml of chloroform is added dropwise at RT to a stirred solution of benzo[b]thiophene (1, 22.4 g, 0.166 mmol) in 340 ml of chloroform. After 2.5 h, the solvent is distilled off and the liquid that remains behind is then distilled under HV (0.16 mbar, 94° C.), yielding 2 (27.7 g, 78%) in the form of a pale yellow solution: $^1$H-NMR (300 MHz, DMSO-$d_6$): 7.39–7.51 (m, 2H); 7.70–7.75 (m, 1H); 7.95 (s, 1H); 7.99–8.04 (m, 1H).

b) Benzo[b]thiophene-3-carboxylic acid 3: A solution of 2 and methyl iodide (14.4 ml, 230 mmol, 1 eq.) in 230 ml of anhydrous diethyl ether is added dropwise to a vigorously stirred suspension of magnesium chips (24.3 g, 575 mmol, 2.5 eq.) in 60 ml of anhydrous diethyl ether in such a manner that the reaction temperature does not exceed 34° C. When the addition is complete, the reaction mixture is boiled under reflux for 30 min. After cooling to RT, 290 ml of toluene are added and carbon dioxide is passed through the mixture for 6 h. The resulting yellow precipitate is dissolved in 400 ml of HCl (4M in water). The phases are separated and the aqueous phase is extracted three times with ethyl acetate. The combined organic phases are extracted four times with 10% sodium carbonate solution, and the resulting aqueous extracts are washed with diethyl ether and acidified with HCl (4M). The precipitate is filtered off, washed with water and dried under HV, yielding 3 (18.4 g, 45%) in the form of white crystals: $^1$H-NMR (300 MHz, DMSO-$d_6$): 7.39–7.55 (m, 2H); 8.05 (ddd, J=7.9, 1.5, 0.6, 1H); 8.49 (ddd, J=7.9, 1.5, 0.6, 1H); 8.61 (s, 1H); 12.29 (s, br, 1H).

c) Benzo[b]thiophene-3-carboxylic acid chloride 4: A mixture of 3 (7.50 g, 42.1 mmol) and thionyl chloride (15.0 ml, 206 mmol, 4.9 eq.) is boiled under reflux for 4 h. The excess thionyl chloride is removed in vacuo and the residue is distilled in a kugelrohr (b.p. 132° C., 0.076 mbar), yielding 4 (7.96 g, 96%) in the form of white crystals: $^1$H-NMR (300 MHz, DMSO-$d_6$): 7.39–7.55 (m, 2H); 7.99 (d, J=7.9, 1H); 8.48 (d, J=7.9, 1H); 8.61 (s, 1H).

d) Benzo[b]thiophene-3-carboxylic acid (1 (S)-hydroxymethyl-2-methyl-propyl)-amide 5a: A solution of L-valinol ((S)-2-amino-3-methyl-1-butanol); 4.41 g, 42.7 mmol) and triethylamine (6.63 ml, 47.0 mmol, 1.12 eq.) in 120 ml of methylene chloride is cooled to 0° C. under nitrogen. A solution of 4 (8.40 g, 42.7 mmol) in 120 ml of methylene chloride is added dropwise in the course of 30 min and the reaction mixture is stirred overnight at RT. The resulting suspension is dissolved in 700 ml of methylene chloride and extracted with 500 ml of hydrochloric acid (1 M). After re-extraction of the aqueous phase, the combined organic phases are dried over sodium sulfate, filtered and concentrated by evaporation. Recrystallisation from methylene chloride/hexane yields 5a (9.30 g, 83%) in the form of white crystals: $^1$H-NMR (300 MHz, DMSO-$d_6$): 0.91 (d, J=7.0, 3H); 0.93 (d, J=7.0, 3H); 1.92 (m, 1H); 3.45–3.55 (m, 2H); 3.84–3.92 (m, 1H); 4.57 (t, J=5.6, 1H); 7.37–7.48 (m, 2H); 7.94 (d, J=9.1, 1H); 7.99–8.02 (m, 1H); 8.34 (s, 1H); 8.39–8.42 (m, 1H).

e) Benzo[b]thiophene-3-carboxylic acid (1 (S)-chloromethyl-2-methylpropyl)-amide 6a: The acid 5a (9.30 g, 35.5 mmol) is dissolved in 145 ml of dichloroethane; thionyl chloride (6.33 ml, 86.1 mmol, 2.43 eq.) is added and the mixture is stirred at 70° C. for 2 h. After cooling to RT, 150 ml of a saturated sodium carbonate solution are added to the resulting solution. The organic phase is separated off and the aqueous phase is re-extracted twice with 160 ml of methylene chloride. The combined organic phases are dried over sodium sulfate, filtered and concentrated by evaporation, yielding 6a (9.68 g, 97%) in the form of white crystals: $^1$H-NMR (300 MHz, DMSO-$d_6$): 0.94 (d, J=6.8, 3H); 0.98 (d, J=6.8, 3H); 1.86–2.04 (m, 1H); 3.75 (dd, J=11.1, 7.9, 1H); 3.85 (dd, J=11.1, 3.8, 1H); 4.00–4.10 (m, 1H); 7.38–7.48 (m, 2H); 8.00–8.04 (m, 1H); 8.35 (d, J=8.5, 1H); 8.37–8.41 (m, 2H).

f) 2-Benzo[b]thiophen-3-yl-4(S)-isopropyl-4,5-dihydro-oxazoline 7a: A mixture of 6a (9.68 g, 34.4 mmol) and a solution of sodium hydroxide (1.44 g, 36.1 mmol, 1.05 eq.) in 250 ml of methanol is stirred at 70° C. for 2 h. The solvent is removed using a rotary evaporator. The residue is taken up in 300 ml of methylene chloride and extracted with 150 ml of saturated sodium hydrogen carbonate solution. The organic phase is dried over sodium sulfate, filtered and concentrated by evaporation, yielding 7a (8.48 g, 100%) in the form of a yellow oil: $^1$H-NMR (300 MHz, CDCl$_3$): 0.99 (d, J=6.7, 3H); 1.11 (d, J=6.7, 3H); 1.80–1.95 (m, 1H); 4.11 (dd, J=15.2, 7.6, 1H); 4.16–4.23 (m, 1H); 4.38 (dd, J=9.1, 7.4, 1H); 7.37–7.52 (m, 2H); 7.82–7.90 (m, 1H); 8.07 (s, 1H); 8.79–8.83 (m, 1H).

EXAMPLE 2

[4(S)-tert-Butyl-2-(2-diphenylphosphanyl-benzo[b]thiophen-3-yl)]-4,5-dihydro-oxazoline 8b Prepared analogously to the procedure for Example 1. Starting from 7b (0.72 g, 2.77 mmol), n-butyllithium (1.9 ml, 3.05 mmol, 1.1 eq.) and chlorodiphenylphosphine (0.51 ml, 2.77 mmol, 1 eq.), 8b (0.64 g, 52%) is obtained in the form of white crystals: $^{31}$P-NMR (124 MHz, CDCl$_3$): –12.4; $^1$H-NMR (300 MHz, CDCl$_3$): 0.81 (s, 9H); 3.90–4.15 (m, 3H); 7.27–7.46 (m, 12H); 7.64–7.69 (m, 1H); 8.56–8.63 (m, 1H).

The starting materials are prepared as follows:

a) Benzo[b]thiophene-3-carboxylic acid (1 (S)-hydroxymethyl-2,2-dimethylpropyl)-amide 5b: Prepared analogously to Example 1d). Starting from L-tert-leucinol ((S)-2-amino-3,3-dimethyl-1-butanol; 0.48 g, 4.07 mmol), triethylamine (0.6 ml, 4.47 mmol, 1.12 eq.) and compound 4 (Example 1c)), 5b (1.12 g, 99%) is obtained in the form of white crystals: $^1$H-NMR (300 MHz, DMSO-$d_6$): 0.93 (s, 9H); 3.46 (ddd, J=15.0, 8.8, 6.1, 1H); 3.67 (ddd, J=15.0, 8.8, 5.3, 1H); 3.90 (ddd, J=8.8, 8.8, 3.5, 1H); 4.48 (t, J=5.7, 1H); 7.34–7.46 (m, 2H); 7.96 (d, J=9.4, 1H); 7.99–8.02 (m, 1H); 8.34 (s, 1H); 8.35–8.40 (m, 1H).

b) 2-Benzo[b]thiophen-3-yl-(4S)-tert-butyl-4,5-dihydro-oxazole 7b: Prepared analogously to the procedure for 6a, Example 1e). Starting from the alcohol 5b (1.12 g, 4.04 mmol) and thionyl chloride (0.7 ml, 9.81 mmol), the oxazoline 7b (0.80 g, 70%) is obtained directly in the form of a colourless oil: $^1$H-NMR (300 MHz, CDCl$_3$): 1.02 (s, 9H); 4.11–4.23 (m, 2H); 4.26–4.35 (m, 1H); 7.37–7.52 (m, 2H); 7.87 (d, J=8.2, 1H); 8.08 (s, 1H); 8.79 (d, J=7.9, 1H).

EXAMPLE 3

2-(2-Diphenylphosphanyl-benzo[b]thiophen-3-yl)-(4S)-phenyl-4,5-dihydro-oxazoline 8c Procedure analogous to Example 1 or 2. Starting from 7c (1.00 g, 3.36 mmol), n-butyllithium (2.3 ml, 3.70 mmol, 1.1 eq.) and chlorodiphenylphosphine (0.62 ml, 3.36 mmol, 1 eq.), 8c (1.22 g, 78%) is obtained in the form of white crystals: $^{31}$P-NMR (124 MHz, CDCl$_3$): –12.4; $^1$H-NMR (300 MHz, CDCl$_3$): 3.96 (dd, J=8.3, 8.3, 1H); 4.56 (dd, J=10.3, 8.3, 1H); 5.34 (dd, J=10.3, 8.8, 1H); 7.04–7.09 (m, 2H); 7.22–7.52 (m, 15H); 7.68–7.72 (m, 1H); 8.60–8.66 (m, 1H).

The starting compounds are prepared as follows:

a) Benzo[b]thiophene-3-carboxylic acid (1 (S)-hydroxymethyl-1-phenyl-ethyl)-amide 5c: Procedure analogous to Example 1d). Starting from L-α-phenylglycinol ((S)-2-amino-2-phenyl-ethanol; 0.70 g, 5.09 mmol), triethylamine (0.8 ml, 5.60 mmol, 1.12 eq.) and 4c (1.00 g, 5.09 mmol), 5c (1.52 g, 100%) is obtained in the form of white crystals: $^1$H-NMR (300 MHz, DMSO-$d_6$): 3.61–3.79 (m, 2H); 4.97 (t, J=5.9, 1H); 5.04–5.18 (m, 1H); 7.20–7.48 (m, 7H); 7.99–8.02 (m, 1H); 8.32–8.40 (m, 1H); 8.48 (s, 1H); 8.76 (d, J=7.9, 1H).

b) 2-Benzothiophen-3-yl-(4S)-phenyl-4,5-dihydro-oxazole 7c: Prepared analogously to the procedure of Example 1e). Starting from the alcohol 5c (1.51 g, 5.09 mmol) and thionyl chloride (0.9 ml, 12.4 mmol), the oxazoline 7c (1.35 g, 84%) is obtained directly in the form of white crystals: $^1$H-NMR (300 MHz, CDCl$_3$): 4.24 (dd, J=8.1, 8.1, 1H); 4.77 (dd, J=8.21, 10.0, 1H); 5.51 (dd, J=10.0, 8.2, 1H); 7.30–7.53 (m, 7H); 7.85–7.92 (m, 1H); 8.22 (s, 1H); 8.87–8.92 (m, 1H).

Reaction scheme for Examples 4 to 6:

rotary evaporator. The crude product is purified by column chromatography (SiO$_2$, diethyl ether) and yields compound 13a (14 mg, 30%) in the form of an oil: $^1$H-NMR (300 MHz, CDCl$_3$): 0.83 (d, J=6.6, 3H); 0.95 (d, J=6.6, 3H); 1.58 (sept, J=6.6, 1H); 3.15–3.45 (m, 3H); 4.00 (s, 3H); 7.20–8.00 (m, 14H).

The starting compounds are prepared as follows:

a) 1-Methyl-1H-indole-3-carbaldehyde 10: Sodium hydride (1.8 g of a 60% suspension in mineral oil, 44.9 mmol) is slowly added to a solution of 9 (indole-3-carbaldehyde; 4.0 g, 27.5 mmol) in THF. The reaction mixture is stirred for 1 h at RT and then methyl iodide (3.34 ml, 55.1 mmol) is added. The reaction mixture is stirred at RT for a further 8 h and then quenched by the addition of water (20 ml). Extraction is then carried out with ethyl acetate. The combined organic phases are dried (sodium sulfate) and the solvent is removed using a rotary evaporator, yielding the N-methylated aldehyde 10 (4.3 g, 98%) in the form of a yellow solid: $^1$H-NMR (300 MHz, CDCl$_3$): 3.87 (s, 3H); 7.27–7.37 (m, 2H); 7.67 (s, 1H); 8.3 (m, 1H); 9.98 (s, 1H).

b) 1-Methyl-1H-indole-3-carbonitrile 11: NH$_2$OH.HCl (3.8 g, 55 mmol) and pyridine (11.1 ml, 137 mmol) are added to a solution of 10 (4.3 g, 27.5 mmol) in ethanol (15 ml) and the mixture is stirred under reflux for 3 h. After

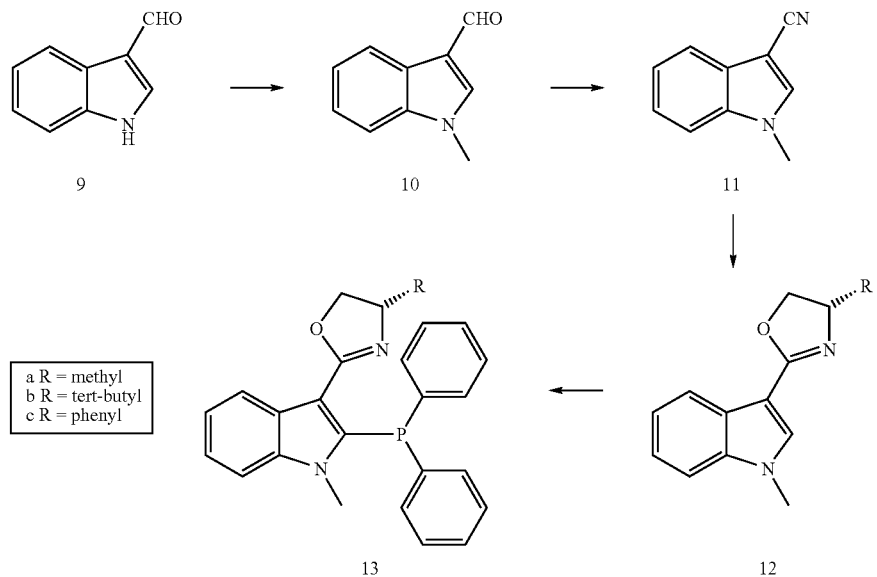

EXAMPLE 4

2-Diphenylphosphanyl-1-methyl-3-[(4S)-methyl-4,5-dihydro-oxazol-2-yl]-1H-indole 13a N,N,N',N'-Tetramethyl-ethylenediamine (56 μl, 0.37 mmol) is added to a solution of 12a (30 mg, 0.12 mmol) in THF (1 ml). The solution is cooled to −78° C. and then tert-butyllithium (1.5M in pentane, 0.25 ml, 0.37 mmol) is added dropwise. Stirring is carried out at −78° C. for 2 h and then chlorodiphenylphosphine (70 μl, 0.37 mmol) is added. The reaction mixture is then slowly heated to RT over a period of 6 h and quenched by the addition of saturated sodium hydrogen carbonate solution. The product is extracted with ethyl acetate. The combined organic phases are dried over sodium sulfate and concentrated using a cooling to RT, the reaction is quenched by the addition of hydrochloric acid (1M). The solvent is evaporated and the residue is extracted with ethyl acetate (3×10 ml). The combined organic phases are washed with HCl (1M), dried over sodium sulfate and concentrated using a rotary evaporator. The residue is caused to crystallise by the addition of ethanol and cyclohexane. The oxime so obtained is filtered off, washed with cyclohexane, dried and then dissolved in acetic anhydride (10 ml). The reaction mixture is stirred in an open reaction vessel for 48 h at 80° C. and then partitioned between ethyl acetate (40 ml) and saturated sodium hydrogen carbonate solution. The organic phase is separated off and the aqueous phase is re-extracted with ethyl acetate. The combined organic phases are dried over sodium sulfate and concentrated by evaporation, yielding 11 (4.2 g, 98%) in the form of a dark-violet oil: $^1$H-NMR (CDCl$_3$, 300 MHz): 3.80 (s, 3H); 7.27–7.37 (m, 2H); 7.67 (s, 1H); 7.27–7.41 (m, 3H); 7.58 (s, 1H); 7.68–7.72 (m, 1H).

c) 1-Methyl-3-[(4S)-methyl-4,5-dihydro-oxazol-2-yl]-1H-indole 12a: Zinc dichloride (ZnCl$_2$) (0.39 mg, 2.88 mmol) is melted in a reaction vessel under HV and then cooled under argon. L-Valinol (0.3 g, 3.16 mmol), 11 (0.45 g, 2.88 mmol) and chlorobenzene (10 ml) are then added to the resulting solid. The mixture is boiled under reflux for 58 h. After cooling to RT, the mixture is diluted with methylene chloride, and saturated sodium hydrogen carbonate solution is added. The mixture is stirred at RT for 1 h and then filtered. The organic phase is separated off, dried over sodium sulfate and concentrated by evaporation. The resulting crude product is purified by column chromatography (SiO$_2$, diethyl ether) and yields 12a (0.35 g, 50%) in the form of an oil: $^1$H-NMR (300 MHz, CDCl$_3$): 0.95 (d, J=6.6, 3H); 1.06 (d, J=6.6, 3H); 1.8 (sept, J=6.6, 1H); 3.81 (s, 3H); 4.03–4.16 (m, 2H); 4.30–4.40 (m, 1H); 7.21–7.34 (m, 3H); 7.68 (s, 1H); 8.23–8.27 (m, 1H).

EXAMPLE 5

2-Diphenylphosphanyl-1-methyl-3-[(4S)-tert-butyl-4,5-dihydro-oxazol-2-yl]-1H-indole 13b The compound is prepared analogously to Example 4, starting from a compound 12b which is prepared analogously to compound 12a in Example 5c).

EXAMPLE 6

2-Diphenylphosphanyl-1-methyl-3-[(4S)-phenyl-4,5-dihydro-oxazol-2-yl]-1H-indole 13c The compound is prepared analogously to Example 4, starting from a compound 12c which is prepared analogously to compound 12a in Example 5c).

EXAMPLE 7

Preparation and Use of a Metal Complex in Transfer Catalysis

The following transfer hydrogenation is carried out in the presence of the ligands mentioned below (Ph=Phenyl):

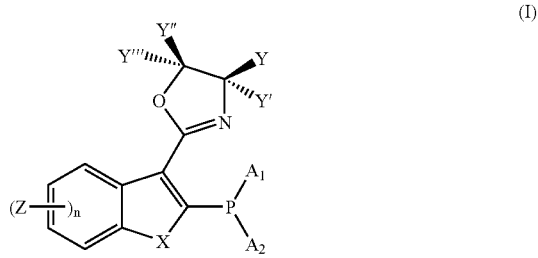

General Catalysis Procedure:

Under argon, 0.010 mmol of [RUCl$_2$(PPh$_3$)$_3$] and 0.013 mmol of 7 are dissolved under reflux (82° C.) in 5 ml of dried, degassed isopropanol. The resulting solution is boiled under reflux for 30 min. A solution of acetophenone (10 mmol) in 3 ml of dried, degassed isopropanol is then added and stirring is carried out for 15 min. The reaction is started by adding a solution of 10 mg (0.25 mmol) of NaOH in 2 ml of isopropanol. After 30 min, the reaction is interrupted, half of the solvent is evaporated and the residue is purified by column chromatography (hexane/ethyl acetate 9:1, v/v).

Results with 7a, 7b and 7c as catalysts:

| | Catalyst | R in the Reaction Scheme for Examples 1 to 3 | Conversion (%) | % ee |
|---|---|---|---|---|
| a) | [RuCl$_2$(PPh$_3$)$_3$] + 7a | isopropyl | 47 | 89 (R) |
| b) | [RuCl$_2$(PPh$_3$)$_3$] + 7b | tert-butyl | 27 | 81 (R) |
| c) | [RuCl$_2$(PPh$_3$)$_3$] + 7c | phenyl | 24 | 70 (R) |

The "ee" (enantiomeric excess) is calculated according to the formula
ee = 100 (X$_R$ − X$_S$)/(X$_R$ + X$_S$), where X$_R$ > X$_S$ wherein X$_R$ and X$_S$ are each the molar amount of the R-form and S-form, respectively, of the product.

What is claimed is:

1. A compound of formula I

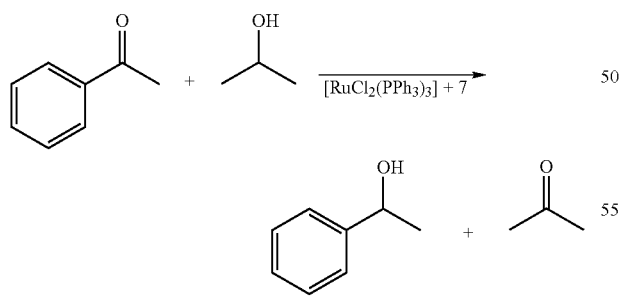

(I)

wherein
X is oxygen, sulfur, selenium or NQ, wherein Q is unsubstituted or substituted aryl, or alkyl or substituted alkyl;

n is 0, 1, 2, 3 or 4;

A$_1$ and A$_2$ are each an organic radical capable of bonding to phosphorus, selected from the group consisting of unsubstituted or substituted alkyl, unsubstituted or substituted aryl, unsubstituted or substituted heterocyclyl, unsubstituted or substituted cycloalkyl, or —N(D)$_2$ wherein D$_2$ is alkyl or substituted alkyl; or A$_1$ and A$_2$ together with the bonding phosphorus atom form a ring, which may be unsubstituted or substituted;

Y, Y', Y" and Y'" are each independently of the other hydrogen or alkyl, substituted alkyl, aryl-lower alkyl wherein the aryl radical is unsubstituted or substituted, and heterocyclyl-lower alkyl wherein the heterocyclyl radical is unsubstituted or substituted, unsubstituted or substituted aryl, or unsubstituted or substituted heterocyclyl, at least one of the radicals Y, Y', Y" or Y'" being one of the mentioned radicals with the exception of hydrogen; and Z, when present, is a substituent, it being possible when a plurality of substituents Z is present for those substituents to be selected independently of one another;

or a mixture of such compounds.

2. A compound of formula IA or IB, falling within the scope of formula I, according to claim 1

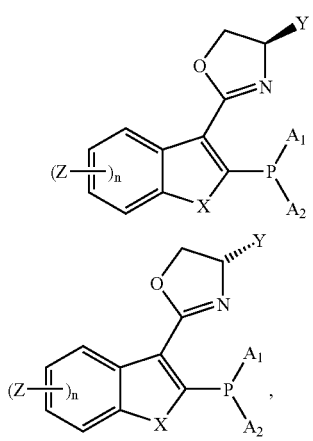

(IA)

(IB)

or a mixture of such compounds, wherein
X is oxygen, sulfur or NQ, wherein Q is unsubstituted or substituted aryl, or alkyl or substituted alkyl;
n is 0, 1, 2, 3 or 4;
$A_1$ and $A_2$ are each an organic radical capable of bonding to phosphorus; or $A_1$ and $A_2$ together with the bonding phosphorus atom form a ring, which may be unsubstituted or substituted;
Y is alkyl, substituted alkyl, unsubstituted or substituted aryl, or unsubstituted or substituted heterocyclyl; and
Z, when present, is a substituent, it being possible when a plurality of substituents Z is present for those substituents to be selected independently of one another.

3. A compound of formula I according to claim 1, wherein $A_1$ and $A_2$ are unsubstituted or substituted alkyl, unsubstituted or substituted aryl, unsubstituted or substituted heterocyclyl, unsubstituted or substituted cycloalkyl, —OD or —N(D)$_2$, wherein D is alkyl or substituted alkyl, and the remaining radicals are as defined in claim 1.

4. A compound of formula I according to claim 1, wherein
X is oxygen, sulfur or NQ, wherein Q is alkyl;
n is 0;
$A_1$ and $A_2$ are each unsubstituted or substituted aryl; and
Y, Y', Y" and Y'" are each independently of the other hydrogen, alkyl or unsubstituted or substituted aryl, at least one of the radicals Y, Y', Y" or Y'" having one of the mentioned meanings with the exception of hydrogen.

5. A compound of formula IA, of formula IB, or a mixture thereof, according to claim 2, wherein
X is sulfur or NQ, wherein Q is lower alkyl;
n is 0;
$A_1$ and $A_2$ are each phenyl;
m is 0; and
Y is lower alkyl or is phenyl.

6. A pure isomer of formula IA or of formula IB according to claim 2.

7. A compound of formula I according to claim 1, selected from the group consisting of
2-(2-diphenylphosphanyl-benzo[b]thiophen-3-yl)-(4S)-isopropyl-4,5-dihydrooxazoline,
[4(S)-tert-butyl-2-(2-diphenylphosphanyl-benzo[b]thiophen-3-yl)]-4,5-dihydrooxazoline,
2-(2-diphenylphosphanyl-benzo[b]thiophen-3-yl)-(4S)-phenyl-4,5-dihydrooxazoline,
2-diphenylphosphanyl-1-methyl-3-[(4S)-methyl-4,5-dihydro-oxazol-2-yl]-1H-indole,
2-diphenylphosphanyl-1-methyl-3-[(4S)-tert-butyl-4,5-dihydro-oxazol-2-yl]-1H-indole and 2-diphenylphosphanyl-1-methyl-3-[(4S)-phenyl-4,5-dihydro-oxazol-2-yl]-1H-indole.

8. A complex of a transition metal which comprises as ligand a compound of formula I according to claim 1 or a mixture of such compounds.

9. A process for the preparation of a complex according to claim 8, wherein one or more ligands of formula I, or a mixture of such compounds, is reacted in an organic solvent under an inert gas atmosphere, at atmospheric pressure at a temperature of from 0° C. to the boiling point of the mixture, with a complex of a transition metal or a solution of a transition metal ion.

10. A process for the preparation of a compound of formula I, or of a mixture of such compounds, as described in claim 1, wherein a compound of formula II, or a mixture of such compounds,

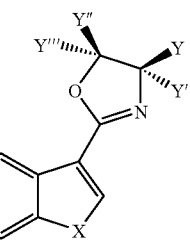

(II)

wherein Z, n, Y, Y', Y", Y'" and X are as defined for compounds of formula I in claim 1, is reacted, after the addition of a metal organyl, with a compound of formula III

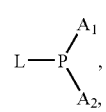

(III)

wherein $A_1$ and $A_2$ are as defined for compounds of formula I in claim 1 and L is halogen, and, if desired, an obtainable compound of formula I, or a mixture of such compounds, is converted into a different compound of formula I, or into a mixture of such compounds, and/or an obtainable isomeric mixture of compounds of formula I is separated into the individual isomers.

11. A compound of formula IA or IB according to claim 2, or a mixture of such compounds, wherein $A_1$ and $A_2$ are unsubstituted or substituted alkyl, unsubstituted or substituted aryl, unsubstituted or substituted heterocyclyl, unsubstituted or substituted cycloalkyl, —OD or —N(D)$_2$, wherein D is alkyl or substituted alkyl, and the remaining radicals are as defined in claim 2.

12. A complex of a transition metal, wherein the transition metal is rhodium, ruthenium, palladium, platinum, iridium, cobalt or nickel, which comprises as ligand a compound of formula IA or IB, as defined in claim 2, or a mixture of such compounds.

13. A method of carrying out a copolymerization, terpolymerisation, catalytic amination or cross-coupling reaction, or asymmetric catalysis reactions selected from the group consisting of asymmetric allylic alkylations, hydrogenations, hydrosilylations, hydroborations, hydroformylations, hydroaminations, Diels-Alder reactions, Grignard cross-coupling reactions, Heck reactions and conjugate-addition reactions, wherein said reactions are conducted in the presence of a complex according to claim 8 as catalyst in said reactions.

* * * * *